May 12, 1964 G. DE RUITER Plant Pat. 2,401
ROSE PLANT
Filed June 13, 1963
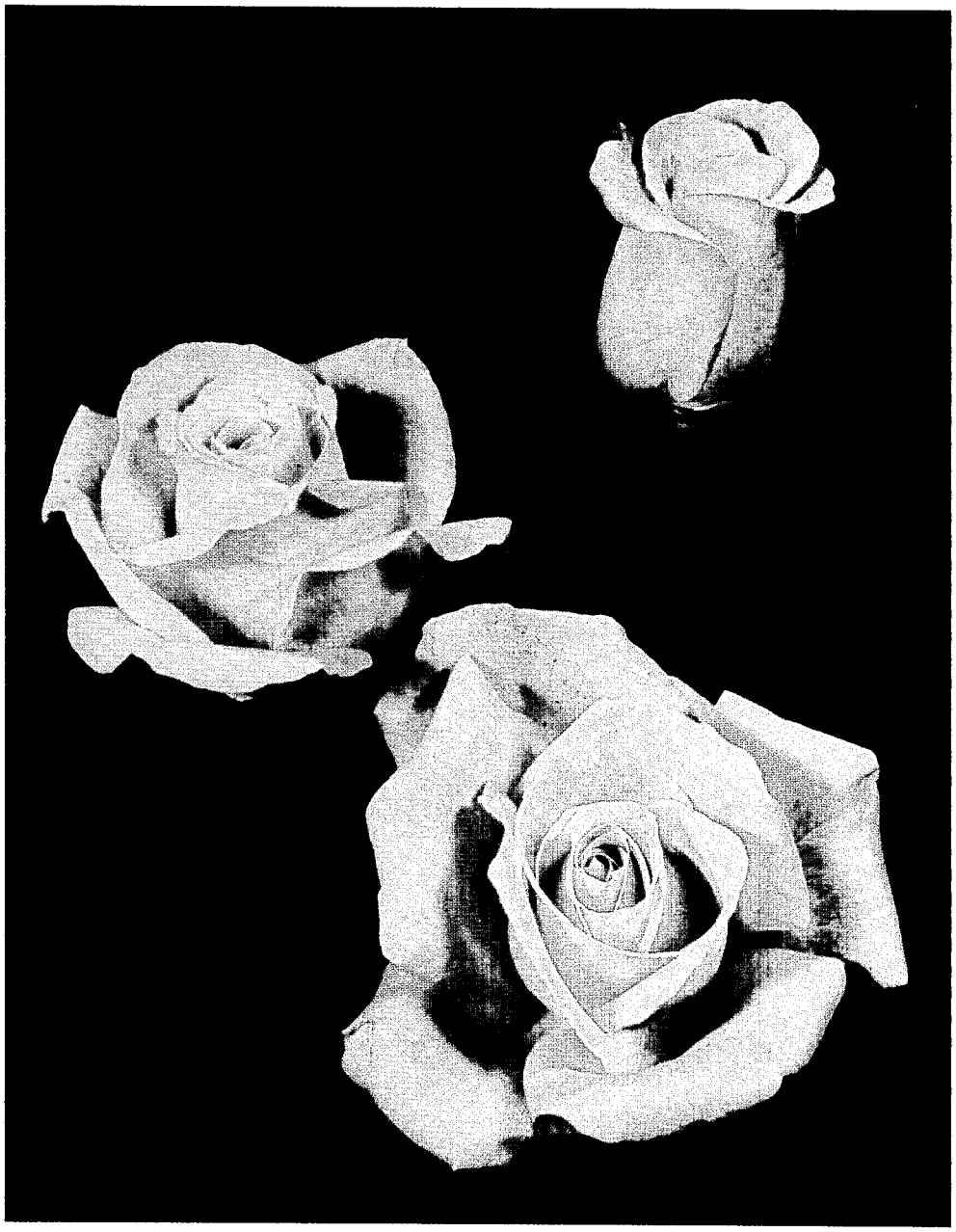
Inventor,
Gijsbert de Ruiter
By: Robb & Robb
Attorneys.

United States Patent Office

Plant Pat. 2,401
Patented May 12, 1964

2,401
ROSE PLANT

Gijsbert de Ruiter, Hazerswoude, Netherlands, assignor to Carlton Rose Nurseries, Carlton, Oreg., a corporation of Oregon Filed June 13, 1963, Ser. No. 287,729
1 Claim. (Cl. Plt.—18)

The present invention relates to a new and distinct variety of rose plant of the hybrid tea class, which was originated by me by crossing the variety known as "The Optimist" (U.S. Plant Patent No. 1,533) with the variety known as "Queen Elizabeth" (U.S. Plant Patent No. 1,259).

As the result of this breeding, I have produced a new and improved rose variety which is especially suitable for the production of cut flowers grown under glass, and which is distinguished from its parents, as well as from all other varieties of which I am aware, as evidenced by the following unique combination of characteristics which are outstanding therein:

(1) A vigorous and upright habit of growth;
(2) Large, dark green foliage;
(3) Freedom from thorns on the flower stems;
(4) A good opening habit of the flower buds when cut in the bud state and kept in water;
(5) Good production of well-shaped double flowers borne on long and strong stems;
(6) Distinctive, attractive and healthy pink flowers; and
(7) Special suitability for cut flower production in greenhouses, as well as good suitability for outdoor flower production under warm and dry climatic conditions.

The distinctions of the new variety from its parents, which are well known, will be obvious from the following description and the accompanying illustrations, without the need of a specific comparison.

In some respects, my new rose variety appears to be slightly similar to the variety recently originated in Europe and known as "Romantica" (unpatented), but my new variety is different in its habit of growth, is better for cut flower production, and produces healthier flowers. Moreover, the variety "Romantica" has very small thorns on its flower stems, while the flower stems of my new variety are free of thorns. The leaves of the new variety are more oblong in shape than those of "Romantica," and a comparison of the reproductive organs shows that my new variety has a much smaller ovary.

Asexual reproduction of the new variety by both grafting and budding, as performed by me at Hazerswoude, Holland, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Wilson Color Chart as prepared in collaboration with the Royal Horticultural Society, except where general color terms of ordinary dictionary significance are obvious:

Type: Tall; greenhouse and outdoor; seedling; for cut flowers.
Class: Hybrid tea.
Breeding: Seedling. Parentage — "The Optimist"× "Queen Elizabeth."
Propagation: Holds its distinguishing characteristics through succeeding propagations by both grafting and budding.

*Flower*

Locality where grown and observed: Hazerswoude, Holland and Aalsmeer, Holland.
Fragrance: From slight to moderate.
Quantity of bloom: Free.
Continuity: Continuous.
Flowers borne: Both singly and several together, particularly when grown outdoors; on strong and long stems.
Bud:
*Peduncle.*—Long; heavy; stiff; almost smooth; with few yellow hairs. Color—medium green.
*Before calyx breaks.*—Size—medium. Form—long; pointed; without foliaceous appendages on the surface of the bud; sometimes with and sometimes without foliaceous parts extending beyond the tip of the bud.
*As calyx breaks.*—Color—Dawn Pink, Plate 523/1.
*As first petal opens.*—Size—large. Form—long; pointed. Opening—opens up well; is retarded by cold weather.
Bloom:
*Size (when fully open).*—Large; from 3½ inches to 5 inches.
*Petalage.*—Very double; from 25 to 30 petals; arranged regularly.
*Form.*—High-centered at first, but becoming open-cupped and rolled outward.
Petals:
*Texture.*—Thick; soft.
*Appearance.*—Inside—satiny. Outside—satiny.
*Shape.*—Outside—round, with one notch. Intermediate—round; scalloped; with apex flat. Inside—round; irregularly scalloped.

This description of a newly opened flower was made from a rose grown in a greenhouse during the month of April at Aalsmeer, Holland:

*Color.*—Outer petal: outside surface—Neyron Rose, Plate 623/2; inside surface—Dawn Pink, Plate 523/1. Intermediate petal: outside surface—Camellia Rose, Plate 622/1; inside surface—Carmine Rose, Plate 621/1. Inner petal: outside surface—Carmine Rose, Plate 621; inside surface—Camellia Rose, Plate 622/1.

This description was made from a rose that was open for three days indoors during the month of April at Aalsmeer, Holland:

*Color.*—Outer petal: outside surface—Dawn Pink, Plate 523/1; inside surface—Camellia Rose, Plate 622/1. Inner petal: outside surface—Neyron Rose, Plate 623/2; inside surface—Dawn Pink, Plate 523.
*General color effect.*—Newly opened flower—soft pink, with salmon shading. Three days open—soft pink, with salmon shading.
*Behavior.*—Drop off cleanly.
*Flower longevity.*—On bush in garden—5 days in July. Cut roses grown in greenhouse and kept at living room temperatures—6 days in April.

*Reproductive Organs*

Stamens: Many; arranged regularly about pistils. Color—yellow, with some being shaded pink or reddish.
Filaments: Short; most with anthers. Color—reddish yellow.
Anthers: Medium size. Color—yellow.
Pollen: Moderate abundance. Color—yellow.
Pistils: Many. Color—light yellow at base, shading to red at top.

Styles: Even; medium length; thin; bunched.
Stigma: Color—yellow-brown.
Ovaries: All enclosed in calyx.
Hips: Globular.
Sepals: Permanent; long; spear-shaped; recurved. Color—Lettuce Green, Plate 861.
Seeds: Few; medium size.

*Plant*

Foliage:

*Leaves.*—Compound of 5 leaflets; normal abundance; medium large size; leathery.

*Leaflets.*—Shape—oval, with apex acute. Base—obtuse. Margin—simply serrate.

*Color.*—Mature: upper surface—normal dark green; under surface—moderately grey green. Young: upper surface—dark bronze; under surface—red.

*Rachis (the supporting stem of the compound leaf).*—Medium size. Upper side—with some hairs. Under side—with some long pointed thorns.

*Stipules.*—Medium length; medium width; with medium long points turning out at an angle of less than 45°.

*Disease resistance.*—Normal resistance for cut roses grown in greenhouses under normal conditions, with mildew and blackspot being easily controlled, as determined by comparison with other varieties grown under the same cultural conditions in Holland.

Growth:

*Habit.*—Bushy; upright.

*Growth.*—Vigorous.

*Canes.*—Heavy.

*Main stems.*—Color—dull grey green. Thorns—several; medium length; hooked downward; with long base. Prickles—none. Hairs—none.

*Branches.*—Color—bright green. Thorns—several; medium length; hooked downward; with long base. Prickles—none. Hairs—none.

*New shoots.* — Color — bright brownish red. Thorns—several; medium length; some straight and some hooked downward; with long base. Prickles—none. Hairs—none.

I claim:

A new and distinct variety of rose plant of the hybrid tea class, substantially as herein shown and described, characterized particularly as to novelty by the unique combination of a vigorous and upright habit of growth, large, dark green foliage, freedom from thorns on the flower stems, a good opening habit of the flower buds when cut in the bud stage and kept in water, good production of well-shaped double flowers borne on long and strong stems, distinctive, attractive and healthy pink flowers, and special suitability for cut flower production in greenhouses, as well as suitability for outdoor flower production under warm and dry climatic conditions.

No references cited.